Figure 1:
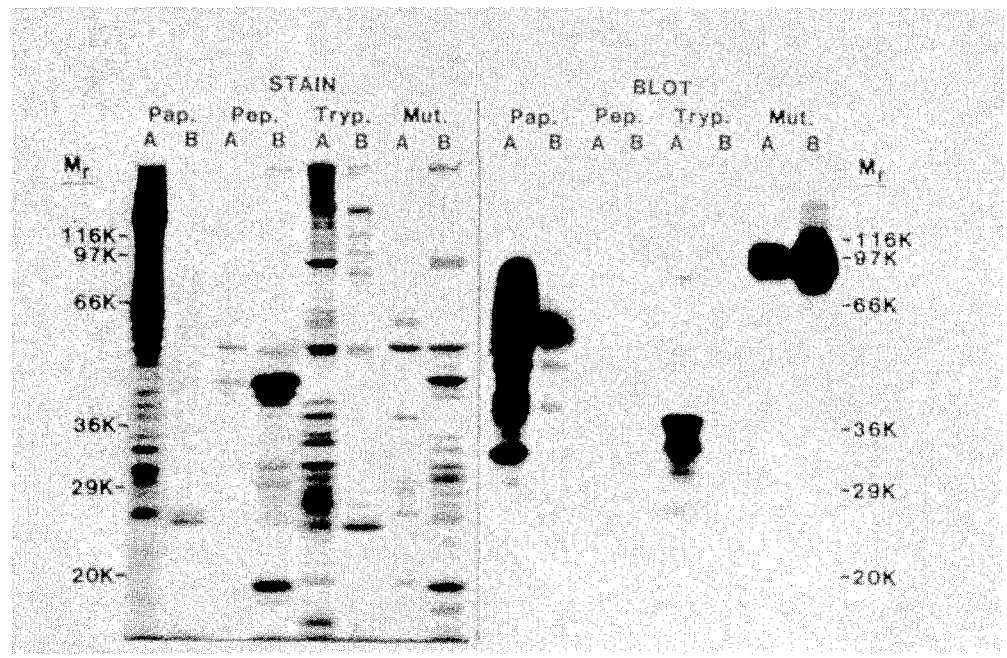

United States Patent [19]

Björck et al.

[11] Patent Number: 4,876,194

[45] Date of Patent: Oct. 24, 1989

[54] **PROTEIN L AND SUBFRAGMENTS THEREOF, WITH IMMUNOGLOBULIN BINDING ACTIVITY, A PROCESS FOR PREPARING THEREOF, REAGENT KIT, PHARMACEUTICAL COMPOSITION AND A *PEPTOCOCCUS MAGNUS* STRAIN**

[75] Inventors: Lars Björck, Södra Sandby; Mats Erntell; Erling Myhre, both of Lund, all of Sweden

[73] Assignee: Hightech Receptor AB, Malmo, Sweden

[21] Appl. No.: 887,926

[22] Filed: Jul. 22, 1986

[51] Int. Cl.[4] .............................................. C12P 21/00
[52] U.S. Cl. ...................................... 435/68; 435/243; 435/259; 435/262; 435/267; 435/803; 435/810; 435/252.1; 514/2; 530/350; 530/412; 530/413; 530/825
[58] Field of Search ................ 436/518; 530/412, 413, 530/825, 350; 435/68, 243, 253, 259, 262, 267, 803, 810; 514/2

[56] References Cited

PUBLICATIONS

Biochemistry, Lehninger, 1978, Worth Pubs., pp. 157–173.

G. Kronvall and R. C. Williams, Jr., The Journal of Immunology, vol. 103, No. 4, Oct. 1969.

A. Forsgren and J. Sjoquist, The Journal of Immunology, vol. 97, No. 6, pp. 822–827.

J. J. Langone, Advances in Immunology, vol. 32, pp. 157–252, 1982.

M. Inganas, Scand. J. Immunol. 13, 343–352, 1981.

L. Bjorck and G. Kronvall, The Journal of Immunology, vol. 133, No. 2, Aug. 2, 1984.

E. B. Myhre and M. Erntell, Molecular Immunology, vol. 22, No. 8, pp. 879–885, 1985.

Bjorck; The Journal of Immunology; vol. 140, No. 4–2/15/88; A Novel Bacterial Cell Wall Protein with Affinity for Ig L Chains[1].

*Primary Examiner*—Robert J. Warden
*Assistant Examiner*—Stephen C. Wieder
*Attorney, Agent, or Firm*—Cushman, Darby & Cushman

[57] ABSTRACT

This invention relates to a new protein L and subfragments thereof with binding activity for all classes of immunoglobulins from different species, a process for preparing the same, a reagent kit, a pharmaceutical composition and strain 312 of *P. magnus*. The process for preparing the protein and subfragments thereof is characterized in that the microorganism *P. magnus* 312 is treated with proteolytic enzymes or mutanolysin.

14 Claims, 3 Drawing Sheets

PROTEIN L AND SUBFRAGMENTS THEREOF, WITH IMMUNOGLOBULIN BINDING ACTIVITY, A PROCESS FOR PREPARING THEREOF, REAGENT KIT, PHARMACEUTICAL COMPOSITION AND A *PEPTOCOCCUS MAGNUS* STRAIN

This invention relates to a new protein called Protein L (L for light chain) and subfragments thereof with immunoglobulin binding activity, a process for preparing the protein and fragments from a strain (312) of the bacterial species Peptococcus magnus, the said strain, a reagent kit and a pharmaceutical composition comprising the protein or the fragments.

Proteins capable of binding to the Fc-fragment of immunoglobulins (Ig) are known and can be used therapeutically and analytically. Thus, Protein A binds to the Fc-fragment of human IgG, except IgG3, but shows poor reactivity with IgG from several animal species such as important laboratory animals i.e. the rat and the goat, which limits the use of protein A as an IgG-reagent. Another protein, protein G, binds to the Fc-fragment of all human IgG-sub-classes and also to many animal equivalents.

This invention relates to a protein which can bind human IgG, IgM and IgA (most probably also IgD and IgE, but these classes have not yet been tested) and also rat, mouse, goat and rabbit IgG (other classes of animal Ig's have not yet been tested). In contrast to other Ig-binding bacterial proteins like protein A and protein G, protein L shows no affinity for the Fc region. Instead, this novel protein binds to Ig kappa and lambda light chains, which means that protein L can be used as a general binding substance for all Ig classes from different animal species. The new protein L has an apparent molecular weight of 95,000 on SDS-PAGE, and it has turned out that subfragments of the protein with lower molecular weights have immunoglobulin binding activity.

Thus the invention relates to a protein L with a capacity of binding the light chains of immunogloabulins IgG, IgM, IgA, IgD and IgE, and to subfragments of protein L with binding affinity for the light kappa and/or lambda chains of all immunoglobulin classes.

The protein and the subfragments thereof can be used as a reagent for binding, separation and identification of immunoglobulins. The invention therefore also concerns a reagent kit containing protein L or subfragments thereof.

The new protein can also be used for absorption of antibodies (immunoglobulins) from the blood of patients with autoimmune diseases. Thus the invention also concerns a pharmaceutical composition containing the protein L or subfragments thereof as active ingredient possibly together with pharmaceutically acceptable adjuvants and excipients.

The protein according to the invention can be produced by treating Peptococcus magnus 312 with enzymes e.g. proteolytic enzymes such as papain, trypsin and pepsin or by mutanolysin. Mutanolysin is preferred. The proteolytic enzymes solubilize protein L but also degrade the protein if the enzyme concentration is too high or the reaction time too long. Thus, the amount of enzyme, pH, reaction time and temperature must be tested to settle optimum conditions. It has turned out that in order to solubilize the whole protein L up to 5 mg papain should be used per 1 ml 10% (vol/vol) cell suspension, preferably up to 1,0 mg/ml and especially up to 100 μg/ml when incubating 1 hour at 37° C. To 1 ml 10% (vol/vol) cell suspension up to 500 μg/ml trypsin should be added, preferably up to 100 μg/ml, when incubating 1 hour at 37° C. and of mutanolysin at least 0,1 U (Sigma containing 1500-3000 U/mg) should be added when incubating 2 hours at 37° C., preferably 0,1 500, especially 0,1-100 most preferably 5-50 U.

In order to solubilize the protein L and degradate it into subfragments with immunoglobulin binding activity papain should be added in a concentration of at least 100 μg/ml cellsuspension, trypsin at least 50 μg/ml and mutanolysin at least 50 U under the same conditions as above.

The optimum concentrations mentioned above might of course change if temperature and incubation time is altered. Also pH influences the optimal concentrations.

The reactions are stopped by adding iodacetamide to papain, benzamidine to trypsin and by adjusting pH to 7.5 for mutanolysin. The strain (312) of Peptococcus magnus 312 from which the new protein can be prepared has been isolated from the urethra of a woman hospitalized with spontaneous abortion at the clinical department of Clinical Microbiology, University Hospital Lund, Sweden.

The invention also concerns Peptococcus magnus strain 312 which has been deposited at ATCC (American Type Culture Collection, 12301 Parklawn Drive, Rockville, Maryland 20852 USA) with the number ATCC 53516 and mutants and variants thereof with binding activity for immunoglobulins from all classes and species.

GROWTH CONDITIONS.

*P. magnus* can be grown in chopped meat-glucose broth (CMG) or in peptone yeast glucose broth. There was no noticeable difference in binding reactivity between bacteria grown in the two media. Further work was performed with bacteria cultured in CMG broth because the anaerobic strains grew better in this medium. After incubation for 36 hr at 37° C. the solid meat particles were removed from the culture by centrifugation at 200 g for 10 min. The supernatant fluid containing the bacteria was transferred to a new centrifuge tube and the organisms pelleted by centrifugation at 2000 g for 10 min. The bacteria where washed twice and suspended in phosphate-buffered saline (PBSA) (120 nM NaCl, 30 mM phosphate, 0.02% sodium azide). The bacterial concentration was determined by centrifugation at 10,000 g for 5 min in capillary tubes in a miniature centrifuge (Microfuge Model 152, Beckman Instruments, Inc., Fullerton, CA). The *P. Magnus* strains analyzed for Ig-binding were identified by morphology, biochemical tests and gas chromatography (Holdeman L.V. Cato E.P. and More W.E.C. (1977) Anaerobe Laboratory, 4th edition, Virginia Polytechnic Institute, Blacksburg, VA). One out of six tested P. magnus strains (strain 312) showed affinity for IgG in binding experiments.

EXAMPLE 1

Peptococcus magnus 312 was grown on blood agar plates at 37° C. for 2 days. The plates were rinsed with 0,05M Tris, pH 7,4 containing 5 mM EDTA (ethylenediaminetetra-acetic acid) and adjusted to 10% by volume. 0.5 ml of the suspension was washed twice with 0.01 M Tris HCl buffer pH 8.0. 27.5 μl L-cystein (1M) and 50 μl (2 mg per ml) papain (Sigma) (100 μg)

was added and the mixture incubated 60 minutes at 37° C. The enzymatic reaction was stopped by addition of iodacetamide to a final concentration of 10 mM. The mixture was centrifuged and the supernatant frozen. The bacteria were killed at 80° C. for 30 minutes and washed with PBSAT (0.12 M NaCl 0.03M phosphate, 0.02% NaN$_3$ 0.05 % Tween® pH 7.2). The bacteria were suspended in PBSAT to 1 % by vol and tested for IgG binding capacity (see below).

EXAMPLE 2

0.5 ml of a 10% (vol/vol) suspension of *P. magnus* 312 in 0,05 M TRIS, pH 7,4 containing 5 m M EDTA was washed twice with 0.05 KH$_2$PO$_4$ pH 5.8. 10 μl 10 mg/ml pepsin (Sigma) (100 μg) was added and the suspension incubated 60 min at 37° C. The enzymatic reaction was stopped by the addition of 7.5 % NaHCO$_3$ to a pH of 7.5. The mixture was centrifuged and the supernatant was frozen. The bacteria were killed by heat as above and washed twice in PBSAT. The bacteria were suspended in PBSAT and made 1% (vol/vol) and IgG-binding capacity was tested as below.

EXAMPLE 3

0.5 ml of a 10% (vol/vol) suspension of *P. magnus* 312 in 0,05 M Tris pH 7,4 containing 5 m M EDTA was washed twice with 0.05 M KH$_2$PO$_4$ containing 0.005M EDTA pH 6.1. 10 μl 10mg/ml trypsin (Sigma) (100 μg) was added and incubated 60 min at 37° C. The enzymatic reaction was stopped with 25 μl 1 0.1 M benzamidine to a final concentration of 5 mM. The mixture was centrifuged and the supernatant frozen. The bacteria were killed by heat as above and washed twice with PBSAT and made up to 1% (vol/vol) in PBSAT and the IgG binding capacity analyzed as below.

EXAMPLE 4

*P. magnus* 312 was suspended in 0,05M Tris, pH 7,4 containing 5 m M EDTA to 10% (vol/vol). 0.5 ml was washed twice with 0.05 M KH$_2$PO$_4$ pH 5.8. Five units of mutanolysin (Sigma) were added. The mixture was incubated at 37° C. for 2 hours. Tne enzymatic reaction was stopped by raising the pH to 7.5 by adding 7.5% NaHCO$_3$ while cooling the test tube on ice. The mixture was centrifuged and the supernatant frozen and the bacteria heat killed as above and washed twice in PBSAT.

BINDING ASSAYS

A. IgG-binding to cells before and after enzyme digestion.

A fixed amount of 125 I labelled (about 10,000 cpm) human IgG was mixed with 200 μl 0.5% bacterial suspension (approx. 2.10$^8$) bacteria in a final vol of 225 μl. PBSA (0.12 M NaCl 0.03 M phosphate 0.02% NaN$_3$ pH 7.2) containing 0.05% Tween®20 and left 30 minutes at 37° C. The suspension was centrifuged, the supernatant sucked off. The radioactivity in the pellets was counted and the binding reported as percent of the radioactivity added. The following results were obtained:

| Radioactivity bound to the bacteria % | |
|---|---|
| 43.1 | before papain digestion |
| 16.1 | after papain digestion |

| -continued | |
|---|---|
| Radioactivity bound to the bacteria % | |
| 38.3 | before pepsin digestion |
| 45.0 | after pepsin digestion |
| 46.1 | before trypsin digestion |
| 39.3 | after trypsin digestion |
| 42.1 | before mutanolysin digestion |
| 35.8 | after mutanolysin digestion |

With papain, trypsin and mutanolysin the IgG binding capacity of the bacteria is reduced, indicating that protein L has been partly solubilized. Under the conditions used here, pepsin does not seem to influence the binding.

B. IgG-binding to solubilized protein L.

Proteins were solubilized from *P. magnus* 312 as described above, with different amounts of papain, pepsin, trypsin and mutanolysin, respectively. The cells were spun down and 50 μl of the supernatants were run on 10% sodium dodecyl sulfate-polyacryl-amide gel electrophoresis (SDS-PAGE). Two gels were run simultaneously. One was stained with Coomassie blue whereas the proteins of the other gel were transferred to a nitrocellulose membrane by Western blotting; (H. Towbin, T. Stachelin and J. Gordon 1979 Proc. Natl.Acad. Sci. USA 76 4350). The membrane was then incubated with $^{125}$I-radiolabelled human IgG. The stained gel and the autoradiograph of the blotted gel is shown in FIG. 1.

LEGEND FIG. 1

One ml of 10% (vol/vol) suspensins of *P. magnus* 312 were treated with 0,1 mg papain (Pap. A), 1,0 mg papain (Pap. B), 0,1 mg pepsin (Pep.A), 1,0 mg pepsin (Pep. B), 0,1 mg trypsin (Tryp.A), 1,0 mg trypsin (Tryp.B), 5 U mutanolysin (Mut.A), and 50 U mutanolysin (Mut.B), respectively.

After the digestions the bacteria were spun down and 50 μl of the supernatants were submitted to SDS-PAGE in 10% gels. Two gels with the same samples were run simultaneously. One was stained with Coomassie blue (stain), one was blotted onto nitrocellulose (blot) and probed with $^{125}$I labelled human IgG. Molecular weight markers are indicated by the arrows.

From FIG. 1 it is apparent that 1 mg Papain (Pap B) is too much and that this concentration of papain breaks down the protein (see pap B in the blot, FIG. 1). The tested amounts of pepsin do not solubilize any IgG binding substances. It is however probable that higher concentrations of pepsin might solubilize the protein. For trypsin, 100 μg gives rise to small IgG-binding peptides (Tryp A in the blot) whereas with 1 mg there is no IgG-binding activity left (Tryp B in the blot). With mutanolysin, both 5 and 50 units solubilize of the protein without degradating it. Among the tested reagents, mutanolysin seems to be the best one, and greater amounts could probably be used. These results indicate that for solubilizing the whole protein L papain should be used in an amount of not more than 1 mg and trypsin not more than 100 ug and mutanolysin up to 50 U or even more when incubated 1 hour, 1 hour, respectively 2 hours at 37° C. respectively with 1 ml of a 10% vol/vol cell suspension.

It is however apparent from FIG. 1 that the subfragments of the protein L (see BLOT, Pap. B, Tryp A) also bind to IgG. In order to solubilize immunoglobulin binding subfragments of protein L from *P. magnus* greater amounts of the enzymes could be used. With the greater amounts of enzyme the protein L is degraded to subfragments.

From the mutanolysin digestion the molecular weight of protein L can be estimated to about 95.000.

PURIFICATION OF PROTEIN L 18.8 ml of a suspension of *P. magnus* 312 10% (vol/vol) in PBS (0.12 M NaCl 0.03 M phosphate) was washed twice with 0.01 M KH$_2$PO$_4$ pH 6.8. 282 μl mutanolysin (1000 U/ml) and 30 μl DNAse was added and the mixture incubated 2 hours at 37° C. in a water bath. The reaction was stopped with 7.5% NaHCO$_3$ to pH 7.5, whereby the test tube was cooled on ice. The suspension was centrifuged and 100 μl of the supernatant frozen for later analysis.

Figure 2:
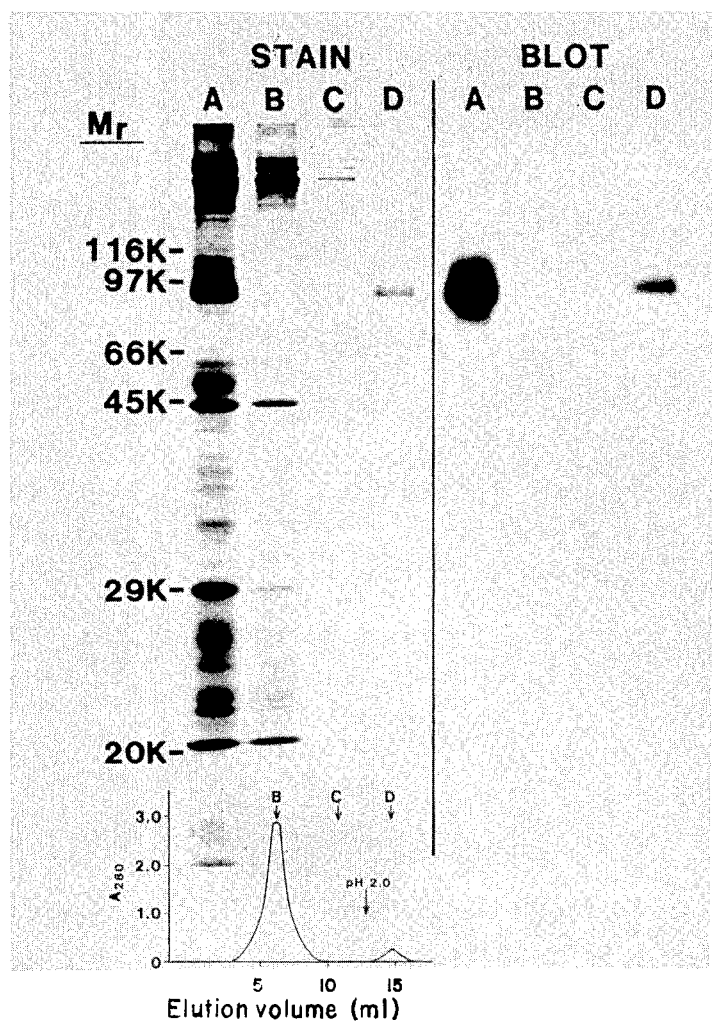

The remaining 1,7 ml was applied to a 2 ml IgG-Sepharose (Pharmacia) column. The sample was allowed to drain into the gel and the column, equilibrated with PBSA, was incubated at room temperature for one hour. Proteins not bound to the column were eluted with 12 ml of PBSA. The absorbed material was then eluted with 6 ml of 0,1 M glycin buffer pH 2,0. During the elution of the column, 0,4 ml fractions were collected at about 15 minute intervals. The protrein content of these fractions was estimated by reading the absorbance at 280 nm (A$_{280}$) (see FIG. 2). Thirty μl of the material applied to the column (A), thirty μl of the peak fraction during elution with PBSA (B), thirty ul of a fraction at the end of this elution (C), and 30 μl of the peak fraction following elution with 0,1 M glycin buffer, pH 2,0 (D) were run on 10% SDS-PAGE (see FIG. 2). One gel was stained with Coomassie blue (stain) and one was transferred to nitrocellulose, probed with $^{125}$I-radiolabelled human IgG and autoradiographed (blot). As shown in the figure, only one protein band was stained in the glycin-eluted peak fraction. Moreover, this band bound radiolabelled human IgG (see blot) and the molecular weight of the band is about 95,000. Thus, a highly purified protein L was obtained. The peak fraction (D) was then dialyzed against PBS and radiolabelled.

RADIOLABELLING OF PROTEIN L

100 μl of the dialyzed fraction (see above) was mixed with 100 μl of $^{125}$I (0,2 mCi diluted in PBS) from Amersham, 20 μl lactoperoxidase (0,25 mmg/ml in PBS) from Sigma and 20 μl H$_2$O$_2$ (30% diluted 1:20 000 in PBS) from Merck. The mixture was incubated for 2 minutes at room temperature. 0,5 ml PBSAT was added and this mixture was run on a PD-10 column (Pharmacia) to separate radiolabelled protein L from free iodine. The fractions corresponding to the radiolabelled protein were pooled and used in binding experiments below.

BINDING PROPERTIES OF RADIOLABELLED PROTEIN L

Polyclonal human IgG (Kabi AB, Stockholm, Sweden) and fragments of this molecule F(ab')$_2$, Fab, and Fc-fragments (prepared from polyclonal and monoclonal IgG as described by Myhre E. B. and Kronvall G. Molec.Immun 17, 1563-1573 and Erntell et al Scand.J.Immun 17, 201-209), human kappa and lambda light chains and heavy chains, prepared from reduced and alkylated polyclonal IgG, human polyclonal IgM and IgA (from Cappel Laboratories, lot nos 17904 and 18447) were applied sto a nitrocellulose membrane using a dot blot apparatus from Schleichen and Schwell. The samples were applied in 100 μl of PBS, srespectively, and the amouints are given in FIG. 3. The membrane was washed in veronal buffered saline containing 0,25% gelatin and 0,25% Tween®-20 for one hour with four 250 ml changes. The nitrocellulose membrane was then probed for 24 hours in this buffer containing 5 x 10$^4$ cpm/ml of $^{125}$I-radiolabelled protein L. After probing, the nitrocellulose was washed four times in 0,01 M EDTA, 1 M NaCl, 0,25% gelatin, and 0,25% Tween®-20 for 15 min each, and allowed to air dry. The niotrocellulose membrane was autoradiographed by exposing to Kodak XAR-5 film with intensifying screen for 3 days at −70° C.

Figure 3:
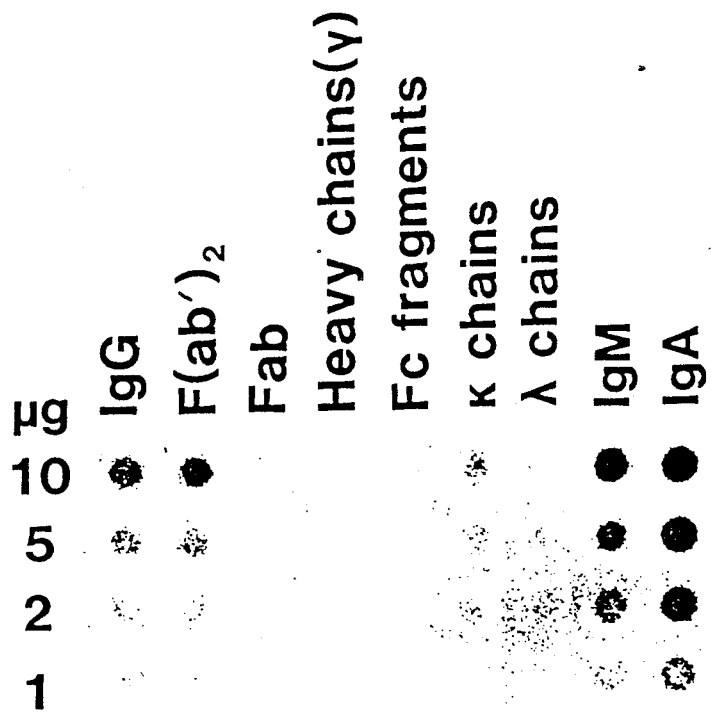

As shown in FIG. 3 radiolabelled protein L is strongly bound to polyclonal human IgG, F (ab')$_2$, IgM and IgA, whereas no reactivity was found for heavy chains or Fc-fragments. Protein L is also clearly bound to kappa light chains whereas the binding to Fab-fragments and lambda light chains is weak. Similar experiments with polyclonal IgG from rat, mouse, rabbit and goat have demonstrated a strong binding a protein L to IgG also from these species (data not shown).

The results of the experiments described here demonstrate that protein L is bound to the light chains of Ig's. As the light chains are shared amoung Ig's belonging to different classes, this means that protein L most probably is bound to all Ig classes.

We claim:

1. A protein having an apparent molecular weight of about 95,000 on sodium dodecyl sulphate-polyacrylamide gel electrophoresis, and subfragments thereof, which protein and subfragments are capable of binding light chains of immunoglobulins IgG, IgM, IgA, IgD and IgE and are substantially free of other proteinaceous materials.

2. A process for preparing a protein having an apparent molecular weight of about 95,000 on sodium dodecyl sulphate-polyacrylamide gel electrophoresis, or subfragments thereof, which protein and subfragments are capable of binding light chains of immunoglobulins IgG, IgM, IgA, IgD and IgE, which process comprises:
   (i) enzymatically solubilizing Peptococcus magnus strain 312; and
   (ii) purifying said protein, or said subfragments, from said solubilized Peptococcus magnus strain 312.

3. The process according to claim 2 wherein said enzyme is a proteolytic enzyme.

4. The process according to claim 3 wherein said proteolytic enzyme is selected from the group consisting of papain and trypsin.

5. The process according to claim 2 wherein said enzyme is mutanolysin.

6. The process according to claim 2 wherein said purifying step (ii) is effected by affinity chromatography utilizing a ligand having an affinity for said protein and said subfragments.

7. The process according to claim 6 wherein said ligand is selected from the group consisting of IgG, IgA, IgM, IgD and IgE.

8. The process according to claim 6 wherein said purifying step (ii) is effected by affinity chromatography on IgG-Sepharose 4B.

9. The process according to claim 8 wherein said enzyme is mutanolysin.

10. The process according to claim 9 wherein at least 0.1U of mutanolysin is added per ml 10% vol/vol cell suspension.

11. The process according to claim 2 wherein a maximum amount of said enzyme added per ml 10% vol/vol cell suspension is 100mg.

12. A pure culture of a microorganism selected from the group consisting of Peptococcus magnus strain 312, ATCC No. 53516, and mutants thereof.

13. A kit for binding, separating, and identifying immunoglobulins, which kit comprises at least one immunoglobulin binding agent selected from the group consisting of protein L and subfragments thereof, together with ancillary reagents.

14. A pharmaceutical composition comprising an effective amount of at least one immunoglobulin binding agent selected from the group consisting of protein L and subfragments thereof, together with a pharmaceutically acceptable carrier.

* * * * *